(12) United States Patent
Zalevsky et al.

(10) Patent No.: US 11,977,148 B2
(45) Date of Patent: May 7, 2024

(54) SYSTEM AND METHOD FOR REMOTE MONITORING

(71) Applicant: BAR ILAN UNIVERSITY, Ramat Gan (IL)

(72) Inventors: Zeev Zalevsky, Rosh HaAyin (IL); Nisim Nisan Ozana, Rehovot (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 818 days.

(21) Appl. No.: 17/051,275

(22) PCT Filed: Apr. 30, 2019

(86) PCT No.: PCT/IL2019/050477
§ 371 (c)(1),
(2) Date: Oct. 28, 2020

(87) PCT Pub. No.: WO2019/211840
PCT Pub. Date: Nov. 7, 2019

(65) Prior Publication Data
US 2021/0063563 A1 Mar. 4, 2021

Related U.S. Application Data

(60) Provisional application No. 62/665,697, filed on May 2, 2018.

(51) Int. Cl.
*G01S 13/88* (2006.01)
*A61B 5/00* (2006.01)
(Continued)

(52) U.S. Cl.
CPC ............ *G01S 13/88* (2013.01); *A61B 5/0015* (2013.01); *A61B 5/024* (2013.01); *A61B 5/0507* (2013.01);
(Continued)

(58) Field of Classification Search
CPC .......... G01S 13/88; G01S 7/415; G01S 13/10; G01S 13/505; G01S 13/582; A61B 5/0507; A61B 5/024
See application file for complete search history.

(56) References Cited

U.S. PATENT DOCUMENTS 8,638,991 B2   1/2014  Zalevsky et al.
2007/0205937 A1  9/2007  Thompson et al.
(Continued)

*Primary Examiner* — Patrick Fernandes
*Assistant Examiner* — Aminah Asghar
(74) *Attorney, Agent, or Firm* — Browdy and Neimark, PLLC

(57) ABSTRACT

A system and corresponding method are described. The system comprises an RF transmission unit comprising an arrangement of one or more transmission antenna elements configured for transmitting radiation in one or more elected frequency ranges toward an inspection region; RF collection unit comprising one or more collection antenna elements configured for receiving radiation in said one or more frequency ranges from at least a portion of said inspection region; and a control system. The control system is configured for receiving and processing data on collected RF signals from the RF collection unit for determining one or more parameters on a at least one object located in said inspection region.

17 Claims, 9 Drawing Sheets

(51) Int. Cl.
  *A61B 5/024* (2006.01)
  *A61B 5/0507* (2021.01)
  *A61B 5/08* (2006.01)
  *G01S 7/41* (2006.01)
  *G01S 13/10* (2006.01)
  *G01S 13/50* (2006.01)

(52) U.S. Cl.
  CPC .............. *A61B 5/08* (2013.01); *A61B 5/7246* (2013.01); *G01S 7/415* (2013.01); *G01S 13/10* (2013.01); *G01S 13/505* (2013.01)

(56) References Cited

U.S. PATENT DOCUMENTS

| | | | |
|---|---|---|---|
| 2014/0148658 A1 | 5/2014 | Zalevsky et al. | |
| 2017/0360357 A1* | 12/2017 | Larson | A61B 5/1115 |
| 2018/0078166 A1* | 3/2018 | Horng | A61B 5/7225 |
| 2018/0263502 A1* | 9/2018 | Lin | G01S 7/415 |

* cited by examiner

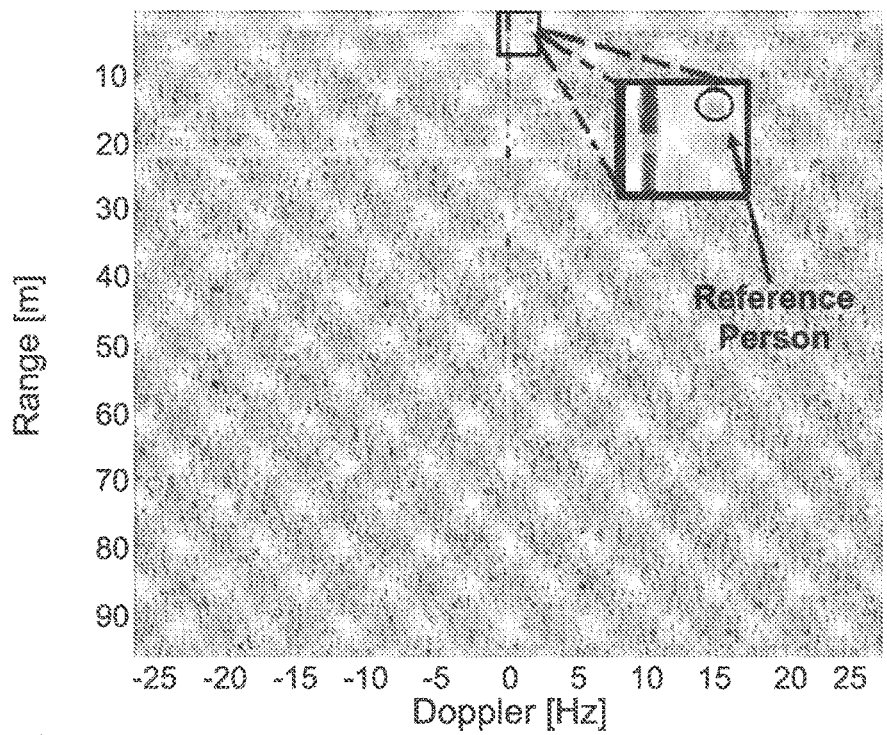
FIG. 7
FIG. 8A
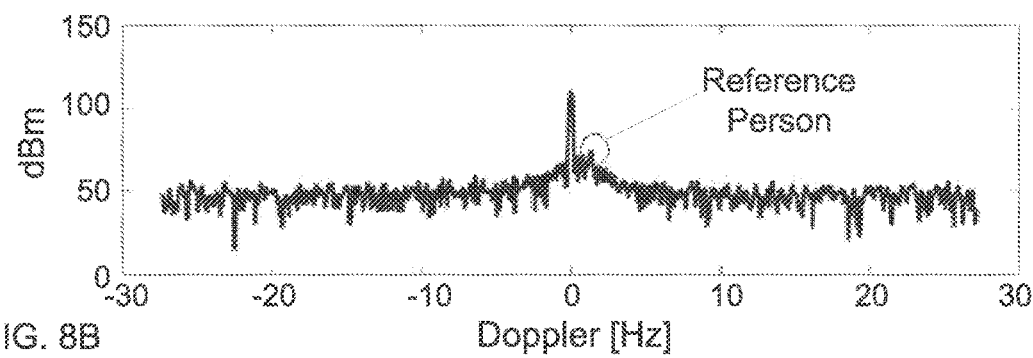
FIG. 8B
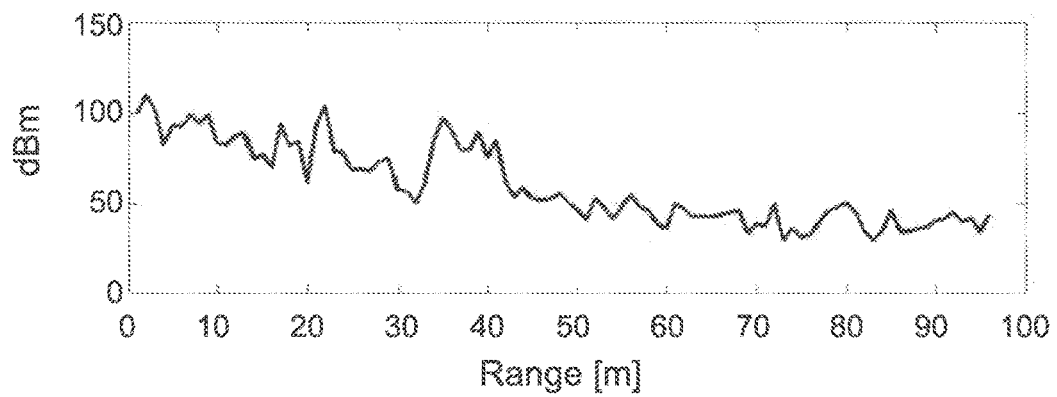

SYSTEM AND METHOD FOR REMOTE MONITORING

TECHNOLOGICAL FIELD

The present invention is in the field of remote monitoring parameters of an object. The invention specifically relates to monitoring of mechanical or biomechanical parameters using RF inspection and monitoring of RF speckles.

BACKGROUND

Biomedical monitoring enables medical personnel to determine medical condition of patients without the need to relay on patient's subjective complaints. Monitoring patients' heart rate, breathing rate and other biomedical parameters has become regular step in patient examination and treatment. Further, biomedical monitoring is also used for monitoring user's athletic performance.

The conventional techniques for monitoring biomedical parameters generally need certain contact with the user. Various optical techniques have been developed, for monitoring and measuring biomedical parameters. Such optical techniques utilize illumination with optical wavelengths and enable detection of various parameters of a user or sample, for example:

US2014148658 presents a system and method for use in monitoring one or more conditions of a subject's body. The system comprises a control system which comprises an input port for receiving image data and data indicative of at least one external stimulation (external field) applied to a portion of the subject's body during collection of the image data therefrom, a memory utility, and a processor utility. The image data is indicative of a sequence of speckle patterns generated by the portion of the subject's body according to a certain sampling time pattern. The processor utility is configured and operable for carrying out the following: processing the image data utilizing the data indicative of the applied external field(s), said processing comprising determining a spatial correlation function between successive speckle patterns in the sequence, and determining a time varying spatial correlation function in the form of a time-varying function of at least one feature of the correlation function indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

U.S. Pat. No. 8,638,991 presents a method for imaging an object. The method comprises imaging a coherent speckle pattern propagating from an object, using an 10 imaging system being focused on a plane displaced from the object.

GENERAL DESCRIPTION

There is a need in the art for novel technique enabling remote monitoring of biomedical and mechanical parameters of a user or sample. The present technique utilizes RF or microwave electromagnetic radiation for monitoring parameters of a sample or user. The use of non-optical electromagnetic radiation enables monitoring from larger distances with respect to optical radiation. Further such use of non-optical radiation omits the need for direct line of sight between the monitoring system and the sample, and enables monitoring through walls or other obstructions.

To this end the present invention provides a monitoring system comprising RF transmission and collection units and a control system. The system is configured for directing RF radiation toward an inspection zone, and receiving returned radiation from one or more objects in the inspection zone. The control system is configured for receiving input data indicative of collected radiation along time of monitoring, and for processing the input data for determining one or more parameters of one or more samples or users located within the inspection region. Generally, the input data is associated with sampling of speckles formed in radiation returning by reflection and scattering from one or more objects. The RF speckles patterns are detected using one or more antenna elements in accordance with spatial and/or temporal variations in intensity or phase of collected RF signals by one or more antenna elements. The present technique utilizes determining variations in the collected speckle patterns for determining data about vibrations or other movements of one or more objects from which the RF radiation is returned. It should also be noted that the use of RF (and/or microwave) radiation enables monitoring is cased where optical monitoring is blocked, e.g. behind walls etc.

Additionally, it should be noted that sensitivity of detection or monitoring using the present technique may be increased if the one or more objects include or carrying metallic elements. Typically, metals and metallic elements have high reflection properties to RF radiation and may accordingly enable detection of small movements using the speckle detection technique described herein. Such increased sensitivity may enable detection of small movements associated with talking voices, e.g. if the subject is wearing metallic helmet/hat or glasses with metallic parts. Thereby enabling the present technique to provide accurate monitoring and listening from large distances and through walls.

The RF transmission unit generally comprises an arrangement of one or more antenna elements and corresponding one or more transmission drivers, and configured for transmitting signal toward a selected inspection region. The signal may be a series of pulses or continuous signal and have frequency range associated between microwave frequency to short or long radio frequency waves. The RF transmission unit may generally be configured for transmitting RF signals toward the selected inspection region utilizing one of phased array configuration of two or more antenna elements, physical configuration of one or more antenna elements (e.g. using dish or structured antenna), or allow omnidirectional transmission. Generally, the inspection region may be defined by angular span of signal transmission. However, the inspection region may be limited by signal collection properties of the RF collection unit.

The RF collection unit comprises an arrangement of one or more antenna elements and configured for collecting RF signals returning from one or more objects in the inspection region for determining spatial time variation of the collected signals. The RF collection unit may also comprise a filtering module configured for filtering collected signals having frequency range similar to that transmitted by the RF transmission unit, and in some configurations for filtering signals received from one or more selected portions of the inspection region (e.g. using phase variations of signals collected by different antenna elements).

The RF collection unit is generally configured for collection of microwave or radio frequency signals having frequency range generally similar to that transmitted by the RF transmission unit. Typically, the RF collection unit may include an arrangement of one or more antenna elements configured for optimized collection of signal arriving from at least a portion of the inspection region. More specifically, the RF transmission unit may transmit signals toward a selected region (e.g. circular region with 15 degrees vertical span, or region of 150 degrees horizontal span and 10 degrees vertical span), while the RF collection unit is configured for optimized collection from only a portion of the region. Such selection of portion of the region may be provided by physical structure of the antenna unit (e.g. using a dish) or, in the case of arrangement of two or more antenna elements, by selection of phase relations between signal portions collected by the different antenna elements.

The RF collection unit is configured for transmitting collected signals, or data thereof, to the control system for filtering and processing of the collected signals. The control system generally comprises at least one processing utility and has access to at least one storage utility comprising one or more pre-stored models for analyzing parameters of one or more object types.

The processing utility receives collected signals with certain sampling rate from the RF collection unit and is configured for processing the collected signals for determining one or more time-correlation functions indicative if slight movements or vibrations of an object within the inspection region. The processing relates to identifying variations in spatial patterns of the collected signals over time. More specifically, RF signals transmitted by the RF transmission unit propagate toward the inspection region and may be reflected from various objects located in propagation path of the signals. The reflected signals propagate back and portion thereof may be collected by the RF collection unit. Generally, potions of the reflected signals may cause self-interference and form speckle patterns in the reflected signal. Such speckle patterns are well known from coherent illumination in optical wavelength ranges, where defocused imaging of a coherently illuminated spot on an object shows secondary speckle patterns and enable detection of nano-vibrations of the region of the object. When using RF radiation, the RF collection unit cannot provide optical imaging of the reflected radiation and can only detect collected radiation using an arrangement of one or more antenna elements. However, using the contrast of the speckle pattern, vibrations in the object reflecting the collected signals cause shifts in the speckle patterns at the detector/antenna elements' plane, which can be detected by processing the collected signals.

Accordingly, the processing may determine spatio-temporal variations in the collected signals, associated with location shifts of speckles formed in the reflected radiation. These variations are typically determined based on amplitude variations and shifting of amplitude variation pattern in collected signals with time. The control system may thus comprise at least one processing utility configured for receiving data on collected signals in certain sampling rate and for processing the data by determining variations between signals collected at certain time t and signals collected at time t+Δt, where Δt is associated with sampling rate of signal collection. The processing utility generally operates for determining such variations between collected patterns for a selected period providing one or more pattern variation functions. These determined pattern variation functions are indicative of small movements or vibrations in one or more objects reflecting the collected radiation.

To determine parameters of the object, the processing utility generally utilizes the pattern variation functions in accordance with one or more models, typically stored in a dedicated storage utility. The one or more models may be object type dependent and include data on relation between vibrations of the object and one or more parameters thereof. Such parameters may comprise breathing rate of a human, heart rate of a human, bio medical and general monitoring of vital signs, engine operation pattern of various vehicles etc. Moreover, the present technique enables monitoring even in cases where one or more walls separate between the system and the subject to be monitored.

Thus, according to a broad aspect, the present invention provides a system comprising:

RF transmission unit comprising an arrangement of one or more transmission antenna elements configured for transmitting radiation in one or more elected frequency ranges toward an inspection region;

RF collection unit comprising one or more collection antenna elements configured for receiving radiation in said one or more frequency ranges from at least a portion of said inspection region; and a control system configured for receiving and processing data on collected RF signals from the RF collection unit for determining one or more parameters on a at least one object located in said inspection region.

According to some embodiments, the one or more parameters comprise one or more parameters associated with micro vibrations of the at least one objects. Additionally, the one or more parameters may comprise parameters in indicative of at least one of heart rate and breathing rate of one or more humans located in the inspection region.

According to some embodiments, the control system may comprise at least one processor configured for receiving and processing said data on collected RF signals, said processing comprises determining at least one time shifting correlation function between RF signals collected at selected sampling rate, said at least one time shifting correlation function being indicative of variations in secondary speckle patterns in RF signals returned from the one or more objects in the inspection region.

The control system may also comprise at least one storage utility comprising pre-stored data on one or more object vibration models; said at least one processor being configured for retrieving data on one or more of said object vibration models and for processing said at least one time shifting correlation function in view of said one or more object vibration models for determining one or more selected parameters of the object.

According to some embodiments, the RF transmission unit may comprise an arrangement of two or more antenna elements configured for transmitting selected RF signal with corresponding phase shifts between the two or more antenna elements to provide transmission of radiation toward a selected inspection region.

According to some embodiments, the RF collection unit may comprise an arrangement of two or more antenna elements, said control system comprises phase relation module configured for receiving collected signals from said two or more antenna elements and for determining phase relations between the collected signals associated with input signal arriving from a selected direction where an object is located.

The control system may be configured and operable for processing input RF signals from said two or more antenna elements and determining at least one time shifting correlation function between RF signals being indicative of spatial changes in collected RF pattern along time, said spatial changes being indicative of variations in secondary speckle patterns in radiation returned from the one or more objects.

Further, the control system may be configured for using polynomial estimation for determining said spatial changes in collected RF patterns associated with spatial distance smaller than distance between said antenna elements.

According to some other embodiments, the RF collection unit may comprise a single antenna element, said control system being configured for determining time variations in collected signal, being indicative of shifting in speckle patterns in radiation returned from the one or more objects.

Generally, the system may utilize RF and/or microwave radiation that is transmitted through various materials enabling monitoring of objects behind walls. It should be noted that according to some embodiments, the RF transmission and RF collection units may utilized pulsed radar transmission scheme enabling identifying location or distance range of the one or more objects in accordance with time difference between transmission of an RF pulse and collection of returning radiation, thus the present technique enables selection of objects to be monitored.

According to one other broad aspect, the present invention provides a method for monitoring parameters of one or more objects, the method comprising:
  providing and transmitting electromagnetic radiation toward an inspection region where the object is located, and collecting returning electromagnetic radiation returning after reflection and scattering from the one or more objects;
  determining time variations in pattern of collected radiation to provide one or more time variations function indicative of shifting in speckle patterns in the collected radiation;
  utilizing one or more object vibrations models and processing said one or more time variation functions for determining one or more parameters of the objects.

Generally, by installing or placing one or more metallic elements on objects to be monitored, the sensitivity of detection by the present technique may be increased. This enables monitoring of small vibrations associated e.g. with acoustic sounds such as talking voices etc. Accordingly, the present technique enables listening to the one or more objects, as well as determining general location (using the pulsed radar technique).

According to yet another broad aspect, the present invention provides software product embedded on a computer readable medium and containing computer code, which when executed by a computer processor causes to the computer to be responsive to input data in the form of collected RF radiation signals, and for processing the input data by determining variations in at least one of amplitude and phase of the collected signals for determining variations in speckle patterns formed in the collected RF radiation, and for determining one or more time variation functions indicative of variations in speckle patterns ion the collected RF radiation, said time variation functions being indicative of one or more parameters of at least one object from which the RF radiation is returned by reflection and/or scattering.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 7 shows Pulsed Doppler radar measurements indicating an experimental configuration for detection of operation and operation frequency of a vehicle's engine;

FIGS. 8A and 8B show Doppler intensity for range of 80 m (FIG. 8A) and range reflection intensity for Doppler frequency shift of 0.01 Hz (FIG. 8B);

FIGS. 12A to 12C show frequency response of detected speckle variation for detection range of 40, 80 and 120 meters respectively when vehicle engine is on.

DETAILED DESCRIPTION OF EMBODIMENTS

Figure 1:
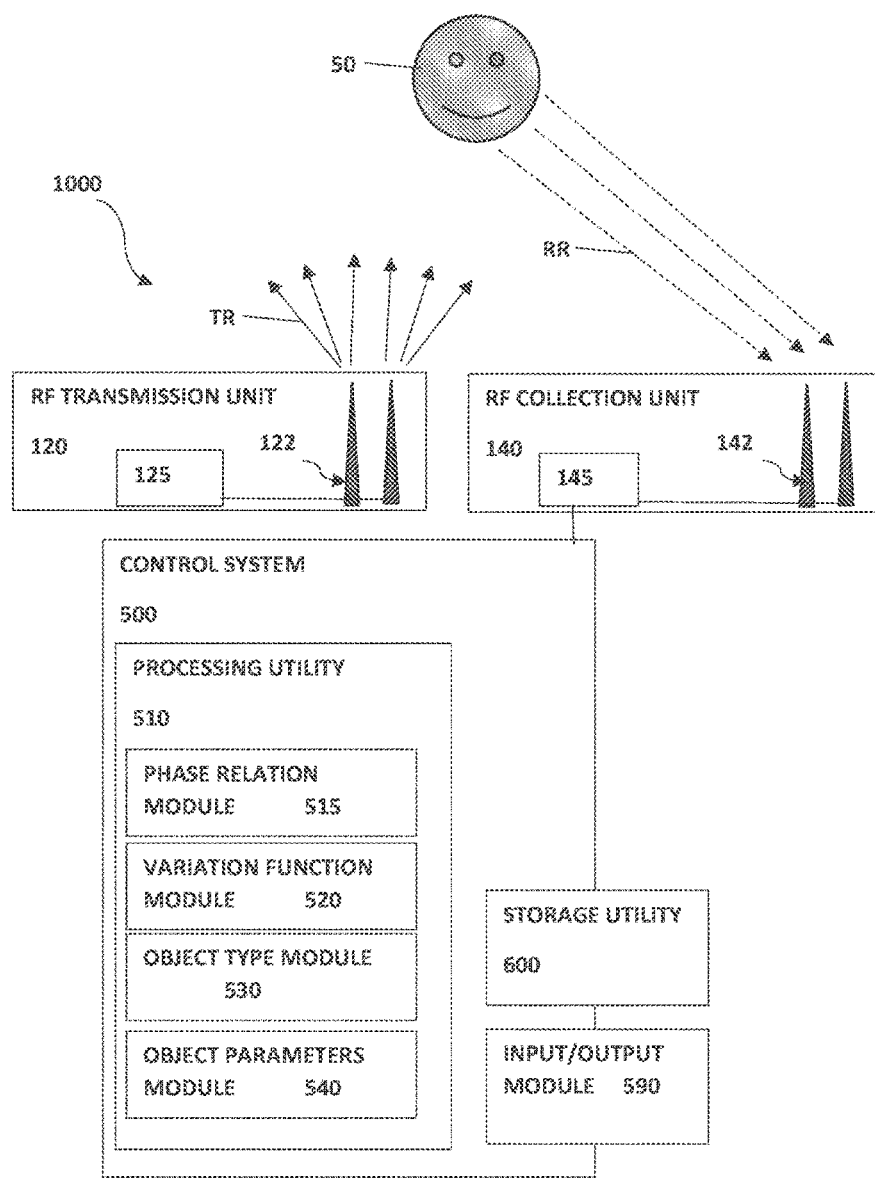
FIG. 1 illustrates schematically a system for monitoring parameters of one or more objects according to some embodiments of the present invention.

Reference is made to FIG. 1 schematically illustrating a system 1000 for monitoring parameters of one or more objects. As shown, the system 1000 includes an RF transmission unit 120, RF collection unit 140 and control system 500. The RF transmission unit 120 is configured for transmitting electromagnetic radiation in microwave and/or radio frequencies toward a selected inspection region. Portion of the transmitted radiation may be reflected from one or more objects, e.g. object 50, and may be collected by the RF collection unit 140. The RF collection unit 140 sends data on the collected signals, using selected sampling rate, to the control system 500 for processing and determining parameters of the object 50 reflecting the radiation signals.

The RF transmission unit 120 includes an arrangement of one or more antenna elements 122 and may also include a driver module 125 (RF transmission driver) configured for conveying signals for transmission by the antenna elements 122. The RF transmission unit is selectively operable for transmitting electromagnetic radiation of selected frequency range, e.g. microwave to radio frequency radiation, toward a selected inspection region. The transmitted radiation may typically be in the form of continuous signal, or a series of pulses having phase coherence between them.

As indicated above, the RF transmission unit 120 includes one or more antenna elements 122. In this connection the selection of number of antenna elements 122 and arrangement thereof, is associated with direction of signal transmission and selection of the inspection region. A single antenna element 122 may be configured to provide omni-directional transmission (e.g. 360 degrees in horizontal plane and 10-40 degrees in vertical plane). Alternatively, such single antenna element 122 may be shaped to transmit radiation toward a selected direction or include a dish for directing majority of the radiation toward the selected inspection region. The use of a plurality of antenna elements 122 in the RF transmission unit 120 enables steering of the transmitted RF radiation using the well-known techniques of phase array antenna arrangements. Accordingly, the use of greater number of antenna elements on the array enables to narrow the transmitted beam toward a smaller and more refined inspection region.

Generally, the RF transmission unit 120 may be provides by input power corresponding to the signal to be transmitted. In some configurations, the RF transmission unit 120 may include one or more RF transmission drivers 125 configured for generating power for the selected signal and providing the required power to the antenna elements 122. The RF transmission driver 125 may typically control phase relations between antenna elements 122 for steering the transmitted beam to selected inspection regions when suitable arrangement of antenna elements 122 is used.

The transmitted signals TR propagate away from the RF transmission unit 120 and in case a portion of the transmitted signals impinge of certain one or more objects 50 located in path of signal propagation, a reflected/scattered signal is returned from the object RR. Generally, at least a portion of the returned radiation RR may be collected by the RF collection unit 140, enabling detection and monitoring of various parameters of the object 50. The RF collection unit 140 includes an arrangement of one or more antenna elements 142, and may also include a filtering module 145, and is configured for collecting radiation reflected/scattered from one or more objects 50 and providing collected radiation data to the control system 500 for processing.

Similarly to the RF transmission unit 120, the antenna elements 142 of the RF collection unit 140 may include one or more antenna elements 142. Accordingly, number and arrangement of the antenna elements 142 may be selected for determining at least a portion of the inspection region for collection of returned radiation RR and detecting and monitoring one or more objects 50 therein. A single antenna element 142 may provide omnidirectional collection, or utilize specific antenna configuration or a corresponding dish for optimizing collection from a specific region. Some configurations may utilize an arrangement of two or more antenna elements providing a phased array configuration. Such configuration enables selection of direction for signals collection using the well-known techniques. Generally, collected signals from the different antenna elements 142 are summed together with phase relations determined in accordance with desired direction for collection of RF signals.

The filtering module 145 may generally be configured for filtering collected signals by frequency for collecting signals having frequency substantially similar to that transmitted by the RF transmission unit 120. Additionally, in some configurations using arrangement of two or more antenna elements 142 and where the signal collection utilizes phased array collection, the filtering module 145 may operates for collecting signals in accordance with suitable phase relations between the antenna elements 142 for collecting radiation arriving from the selected inspection region.

The RF collection unit 140 transmits data on collected signals to the control system 500 for processing and determining parameters of one or more objects 50 reflecting the transmitted radiation. The control system may generally be configured as a computing system including one or more processing utilities 510, storage utility 600 and input/output communication module 590. The control system 500 is typically configured for operating the RF transmission unit 120 for transmitting RF radiation to a selected inspection region and for receiving collected RF radiation returning from one or more objects 50 in the inspection region from the RF collection unit 140. The processing utility 510 is configured for receiving digital or analog data on the collected signals RR and for processing the collected signals by determining signal variations associated with shifting of RF speckles in the reflected radiation RR.

To this end the processing utility 510 may include one or more hardware or software modules configured and operable for performing selected processing tasks. For example, the processing utility may include phase relation module 515 configured for determining phase relations between signal portions collected by different antenna elements 142 for steering RF collection to a selected portion of the inspection region (used in configurations where the filtering module 145 is not used). Additionally, the processing utility includes variation function module 520, object type module 530 and object parameters module 540.

The variation function module 520 is configured for determining spatio-temporal variations in the collected radiation RR pattern for determining shifting of RF speckles in the collected radiation. In this connection, portion of the relatively coherent RF radiation transmitted by the RF transmission unit 120 is scattered from one or more objects 50 in the inspection region forming returned radiation RR. Due to self-interference, the returned radiation RR carries speckle patterns formed by regions of constructive and destructive interference regions. Vibrations of the object 50 cause shifts of the speckle pattern resulting in changes in intensity of collected radiation in the case of single collection antenna element, or shifts in intensity patterns when array of antenna elements is used for collection. A relation between vibrations/movements of the object and shifts in the speckle patterns can be described by $$\beta = \frac{4\pi \cdot \tan\alpha}{\lambda} \cong \frac{4\pi\alpha}{\lambda}$$

where $\beta$ is the shift in speckle pattern, determined by shift in correlation between collected radiation patterns, $\alpha$ is the angular shift of a surface of the object, and is the used radiation wavelength. Further, spackle size may generally be of the order of one to a few wavelengths, and accordingly an array of antenna elements may preferably be configured to be of physical size of a few wavelength or more. The Variation function module 520 is configured for determining shifts in speckles patterns along time for determining one or more variation functions, indicative of vibrations, or small movements, of the object 50.

In this connection, it should be noted that the use of array of two or more antenna elements 142 of the RF collection unit may generally provide improved results over the use of a single antenna element. This is as the number of antenna elements of the array sample the collected radiation RR at two or more different locations enabling to detect shifting in speckle patterns. For example, one or more of the antenna elements of the array may detect lower signal intensity as it is in dark region of the speckle pattern, while antenna elements from different sides thereof may detect signals of opposite phases. In this case, a shift in the speckle pattern may shift the dark region to vicinity of another antenna element showing spatial shift in the collection radiation pattern along time. Thus, the variation function module 520 may determine one or more variation functions by determining correlations between collected radiation patterns by the array of antenna elements. When a single antenna element is used by the RF collection unit 140, shifts in the speckle pattern may be detected as variations in intensity and phase of collected radiation, corresponding to times when the dark regions of the speckle pattern overlap temporarily with the antenna element.

Generally, in some configuration, correlation between collection instances of radiation by an array of antenna elements 142, may utilize super resolving techniques. Such super resolving technique may enable determining shifts smaller than distance between antenna elements of the array for increasing sensitivity of monitoring.

The determined one or more variation functions is generally indicative of vibrations or small repeating movements of the object 50. To determine desired object parameters, the one or more variation functions are processed in accordance with additional data about the object, provided by the object type module 530. Generally, the object type module 530 may receive data about type of the object (human, animal, vehicle etc.) by receiving input data. Such input data may be provided by an operator, additional (e.g. optical) inspection unit, or in accordance with additional processing of the returned radiation RR for determining size shape and type of the object 50.

Data on the object type and the one or more variation functions is transmitted to the object parameters module 540 that may utilize pre-stored data about relations between certain object parameters and vibration pattern of the object for determining object parameters. The object parameters module 540 may thus access corresponding sectors of the storage utility 600 to retrieve data from stored data base in accordance with object type.

Figure 2:
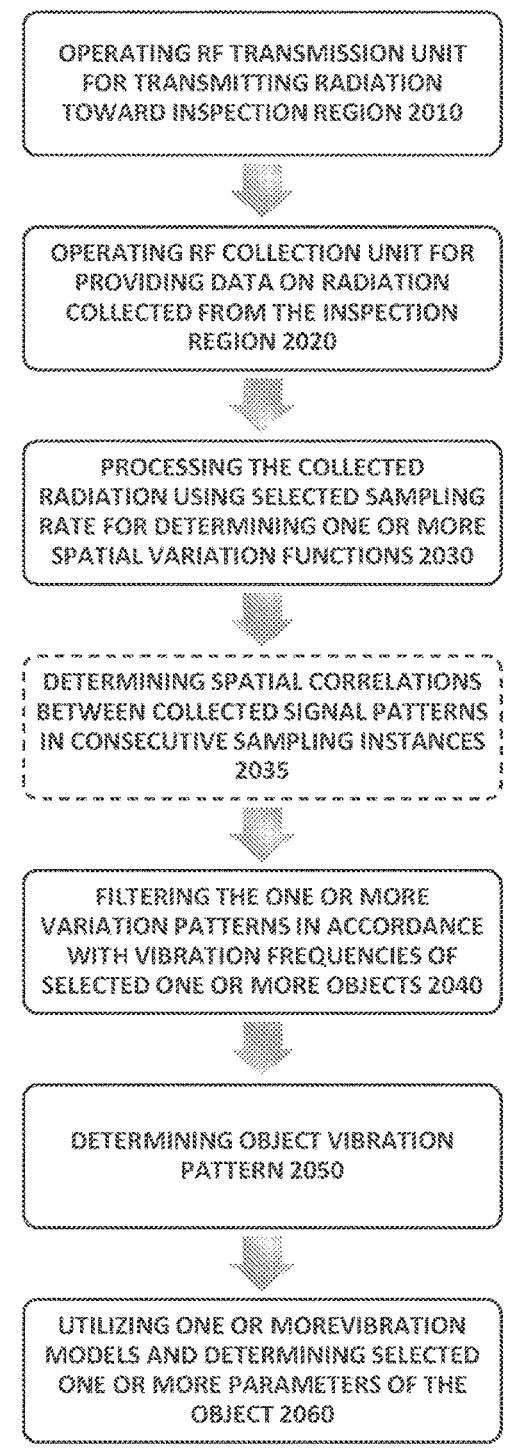
FIG. 2 shows flow diagram illustrating a technique for monitoring parameters of one or more objects according to some embodiments of the present invention.

Reference is made to FIG. 2 illustrating operation of the present technique in a way of a flow diagram. As shown, the present technique utilized operating a transmission unit for transmitting RF radiation toward a selected inspection region 2010. This may be done by transmitting an operation command and suitable power signal to at least one antenna element. Additionally, the technique includes operating a collection unit for collecting radiation returned/reflected from the inspection region 2020, and processing the collected radiation signals for determining at least one variation function 2030 associated with shifts of RF speckles in the collected radiation pattern. Generally, the processing may include determining spatial correlations between collected radiation patterns of consecutive collection instances 2035, which is generally more suitable when the radiation collection utilizes array of antenna elements. Typically, the technique may further apply selected filtering to the determined correlation function 2040 for identifying variations associated with one or more selected parameters. Based on the filtered variations, the technique may further determine data on vibrations pattern of the object 2050, and utilizing one or more pre-stored or predetermined models, to determine one or more selected parameters 2060 such as operation scheme of mechanical system, heart rate, breathing rate and other biomedical parameters etc.

It should be noted that the above describe technique may be utilized as a software product embedded on a computer readable medium. The software product includes computer code associated with instruction for performing the technique as exemplified in FIG. 2.

The inventors of the present invention have performed several exemplary experiments for demonstrating operation of the present technique. One exemplary configuration utilizes transmission of electromagnetic radiation at frequency of 2.4 GHz using two antenna elements transmitting at common phase. A single collection antenna was used for collecting back scattered RF radiation, returned from a human subject. Transmitting and receiving antenna elements are placed at distance of 90 cm between them and at distance of 180 cm from a position where the subject sits. Changes in collected radiation were measured for determining changes in the speckle patterns of radiation scattered from the subject. In this experiment, the returning radiation was collected by a single antenna element. As indicated above, the use of single antenna elements enables detection of shifts in a speckle grain, generally proportional to wavelength (12.5 cm in the case of 2.4 GHz radiation).

Figure 3A:
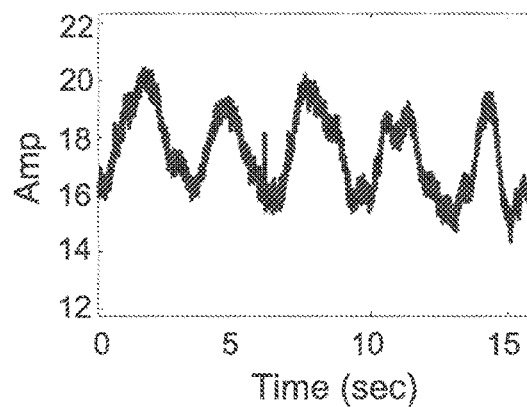
FIGS. 3A and 3B show experimental results indicative of breathing rate of a human subject when asked to breath normally (FIG. 3A) and when asked to hold his breath (FIG. 3B) using a technique according to some embodiments of the present invention.
Figure 3B:
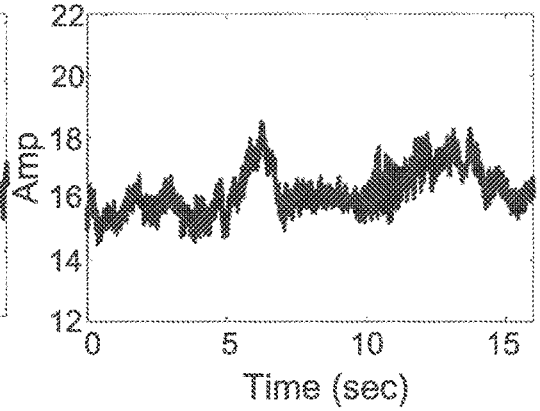

For detection of biomedical parameters of the subject, the set of measurements was divided into tasks. During the first task, the subject was asked to breath normally, and during the second task, the subject was asked to hold his breath. FIGS. 3A and 3B show the determined variation function, determined in accordance with intensity variations of the collected radiation. FIG. 3A shows collected radiation when the subject is breathing normally and FIG. 3B shows the collected radiation when the subject was holding his breath.

Figure 4A:
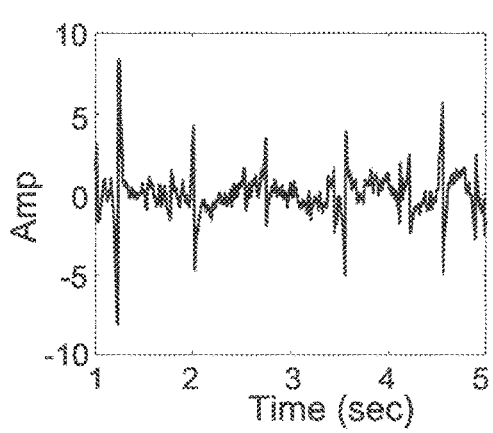
FIGS. 4A and 4B show experimental results indicative of detection heart rate of a subject by monitoring RF speckles using intensity or phase variations respectively according to some embodiments of the present invention.
Figure 4B:
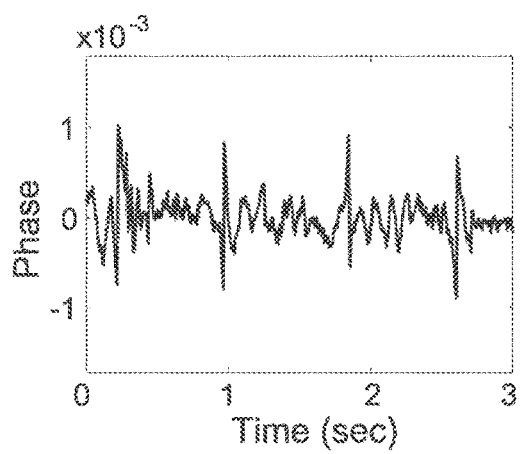

In another test using the same configuration, the collected radiation was filtered by band-pass filtering for detection of heart rate. FIGS. 4A and 4B show filtered variation determined based on amplitude changes and phase changes of collected radiation respectively. As shows, the determined variations provide heart rate data of the subject.

Figures 5A, 5B:
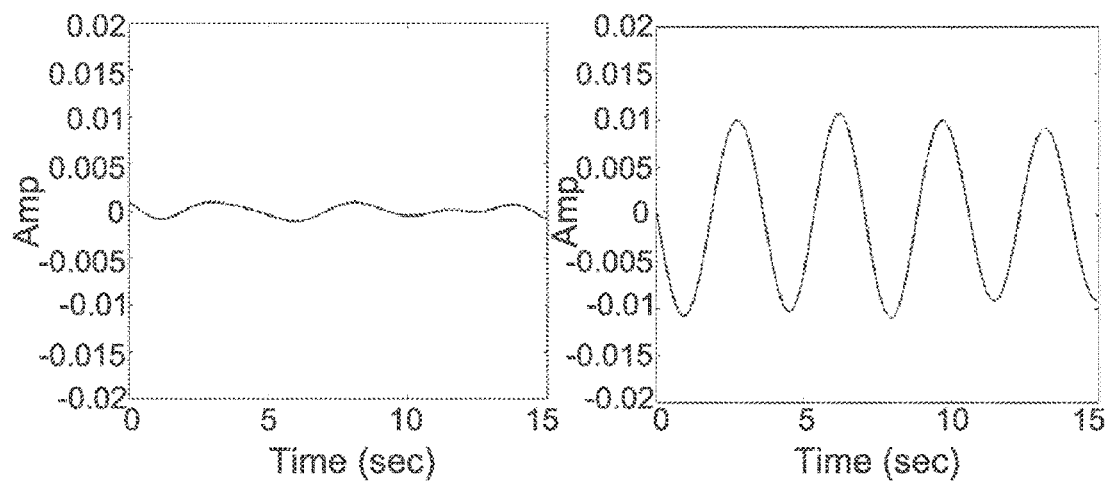
FIGS. 5A and 5B show experimental results indicative of monitoring breathing rate of a human subject through a wall when asked to hold his breath (FIG. 5A) and when asked to breath normally (FIG. 5B) using a technique according to some embodiments of the present invention.
Figure 6:
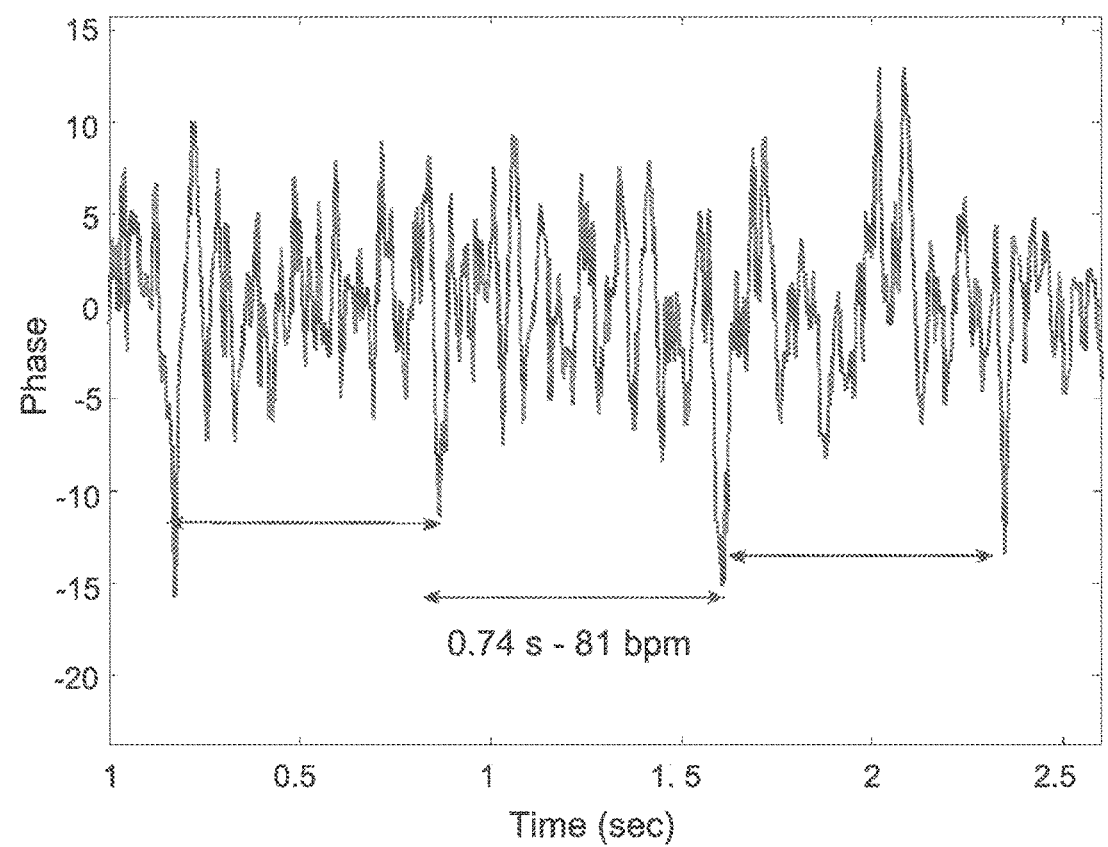
FIG. 6 shows experimental results indicative of detection of heart rate of a subject through a wall using a technique according to some embodiments of the present invention.

The use of RF and/or microwave frequencies enables monitoring parameters of object located where optical (visible or IR) frequencies are blocked. FIGS. 5A and 5B as well as FIG. 6 show monitoring results substantially similar to those of FIGS. 3A and 3B and 4A, while being obtained with a block wall located between the antenna elements and the subject location.

More specifically, in another run of the above describe monitoring configuration, the subject is seated at distance of 100 cm from the antenna elements (transmitting and receiving antenna elements) with a regular internal wall (hollowed blocks) located between the antenna elements and the subject. FIGS. 5A and 5B show monitoring of breathing rate based on filtering variation in collected radiation by band-pass between 0.2-0.33 Hz. FIG. 5A shows monitoring when the subject was asked to hold his breath and FIG. 5B shows monitoring when the subject was asked to breath normally. As shown the breathing action is visible as variations in amplitude of detected signals.

Filtering the determined variation of signal amplitude to higher frequencies, enables detection of heart rate activity of the user. This is shown in FIG. 6 showing clear peaks of detected amplitude variation at frequency corresponding to 81 beats per minute, or 0.74 s between peaks on average. These results illustrate the ability for through-wall detection of biomedical parameters using the present technique as described herein.

In an additional experiment, RF frequency pulses were used for monitoring operation of an automotive vehicle. In this experiment the radiation transmitter used provides output radiation at frequency of 10 GHz. The vehicle was monitored under two conditions, first with its engine on and again with the engine off. An antenna array was used for collection of returning radiation and the returning pulses were stored in a range bin (discrete data elements received from the reflected radar signal) and processed by applying an image correlation algorithm. The processing of the collected radiation data was aimed at determining vibrations of the vehicle associated with operation state of the engine thereof, and for determining vibration frequency of the vehicle.

Generally, as mentioned above, greater frequency of the transmitted radiation may enable higher sensitivity as appears from the relation between speckle shifts $\beta$ and movement $\alpha$ of the object (due to the wavelength $\lambda$).

In this exemplary test, a vehicle was positioned 80 meters for location of transmission unit and collection unit. The transmission and collection units were provided by an X-band, phased array pulse-Doppler radar unit. Each radar section has a Transmitter (Tx) and Receiver (Rx) modules connected directly to the antenna arrangement. The antenna arrangement is a phased array antenna consisting of 16 radiating elements. The antenna array typically utilizes the 16 antenna elements for providing combined beam that can scan in the horizontal (azimuth) direction. However, in this test, the scanning option was disabled, and the antenna arrangement used only eight antenna elements for transmission and 8 antenna elements for collection while operating the different channels simultaneously.

The transmitted beam has vertical (elevation) 3 dB beam width of 10 degrees, and vertical (azimuth) 3 dB beam width of about 100 degrees. The beams were separated by 0.5 degree and the pulse width was 0.1 msec with a dwell time (illumination time on target) of 100 msec. Generally, the vehicle was monitored at distances ranging between 50 and 120 meters and specifically measured at distance of 80 meters, at two different engine operation states, one being off and the other one being on.

The received pulses were measured and processed for extracting pattern of secondary speckles reflected from the vehicle and to determine rate of vibration of the vehicle when the engine was on. Prior to each measurement, a person walked at the targeted site next to the vehicle to provide a reference for detecting the vibration of the vehicle. Generally, the collected signals allow discrimination between the movements of a person and a stationary vehicle as the signal returning from the target was measured using a Pulse-Doppler Radar providing strength of the received pulse as a function of the target's movement with respect to the radar.

The principle behind the Pulsed-Doppler Radar is that it is used to calculate the range to targets by measuring the elapsed time between sending a radio pulse and receiving the reflection from the object. The Radar system may also utilize the Doppler Effect, where the target's movement produces a frequency shift on the signal reflected from the moving target. As the target moves between each transmitted pulse, the returned signal has a phase difference or phase shift from pulse to pulse. As a walking person moves, while the car vibrates but does not move, the amplitude of person's Doppler frequency will be higher than that of the vehicle, thus enabling it to be used as a relative reference signal detected by conventional known techniques.

Generally, the use of Pulsed-Doppler signal in this case is provided for extraction of desired target signals out of the surrounding noise or the clutter (unwanted echoes). It should be noted that the present technique may determine vibrations and parameters of an object without the need to identify exact location of the object as shown in the above test. For simplicity, FIG. 7 shows detection matrix provided by Pulsed-Doppler detection, the matrix shows the reference person located next to a vehicle at distance of about 80 meter. In this matrix, the vertical axis represents distance from the antenna unit and the horizontal axis shows Doppler shift of reflected signal. FIGS. 8A and 8B show section cuts of the detection matrix measured when the vehicle's engine is off. FIG. 8A shows Doppler shift variation detected around distance of 80 meters showing reflection from the static vehicle with no shift and small peak relating to the moving reference person. FIG. 8B shows range section along the Doppler range axis associated with static targets (about 0.01 Hz). As seen from these measurements, the conventional Doppler technique enables detection of moving targets while static targets are generally invisible to the Doppler Radar.

Figure 9A:
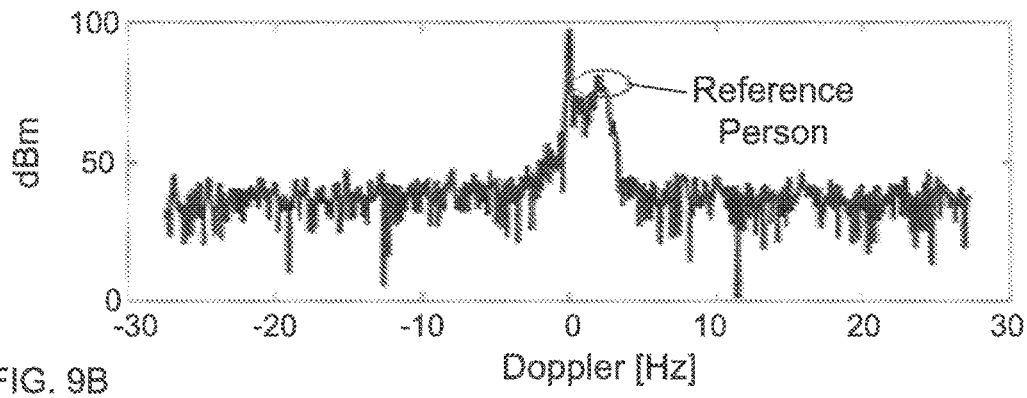
FIGS. 9A and 9B show detected targets by Doppler shifts at distance of 80 m (FIG. 9A) range section along the Doppler range axis associated with static targets (about 0.01 Hz) (FIG. 9B)
Figure 9B:
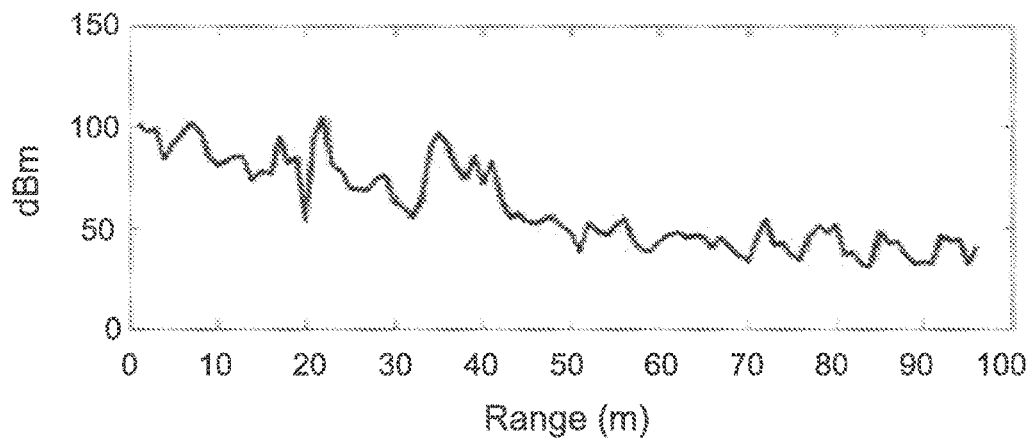

Detection of the vehicle with its engine on using the Pulsed Doppler technique provides similar results, as shown in FIGS. 9A and 9B. FIG. 9A shows detected targets by Doppler shifts at distance of about 80 meters, showing peak associated with the reference person and high reflection with no Doppler shift. FIG. 9B shows range section along the Doppler range axis associated with static targets (about 0.01 Hz), providing substantially similar results. This is to be expected as the vibrations associated with engine operation do not cause large scale movement of the vehicle and accordingly do not cause Doppler shift of reflected radiation.

To provide detection of vibrations of the vehicle, indicating operation state of the engine thereof, the inventors have conducted the test according to the above describe technique. The collected reflection signals were processed by extracting the raw data of collected signals from specific range, and processing the collected raw signals from the different (eight) collection antenna units. The processing was based on determining 1D correlation vector between two adjacent collection instances (associated with digitizing or sampling rate). From the correlation vectors, peak locations were extracted for generating temporal variation of the peak correlation location (corresponding to variation function). Based on the temporal variation of the correlation peak, frequency response of the peak location was determined to identify operation/vibration frequency of the vehicle. This process was repeated for different range values including 40 meters, 80 meters and 120 meters from the radar.

Each of the distance measurements contained 500 different temporal signal samples, each containing a 1-D vector of 8 bits associated with radiation collected by one of the antenna elements. Correlations between the different vectors were determined for identifying speckle pattern shifts based on location of the correlation peak. As indicated above, these shifts are indicative of movement of the target using the relation:

$$\beta = \frac{4\pi \cdot \tan\alpha}{\lambda} \cong \frac{4\pi\alpha}{\lambda}$$

Figure 10:
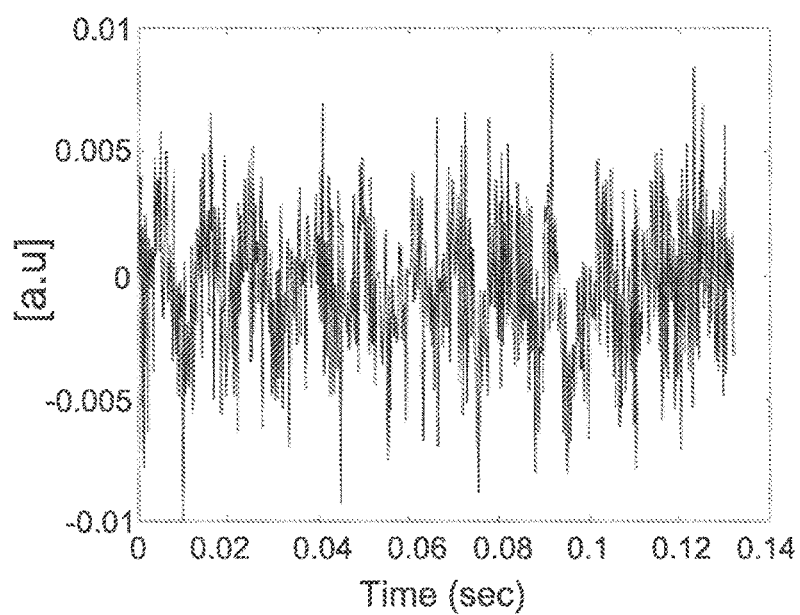
FIG. 10 shows measure correlation shifts between collected radiation patterns associated with speckle pattern variation returning from detection range of 80 m.

Reference is made to FIG. 10 showing temporal vibrations of the vehicle while having engine on, as determined by correlation of the collected signals. The y-axis represents arbitrary units associated with shifts of the RF speckle patterns.

Figure 11A:
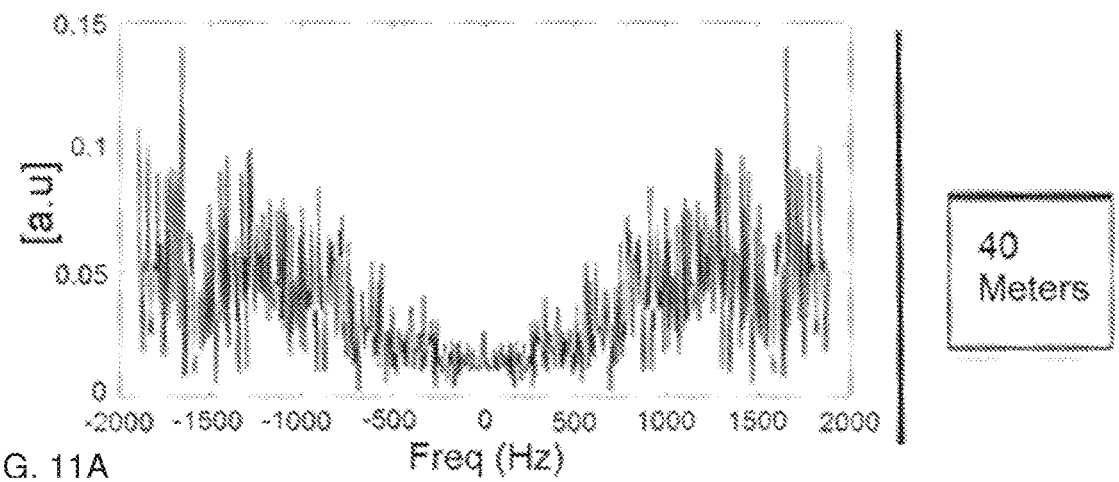
FIGS. 11A to 11C show frequency response of detected speckle variation for detection range of 40, 80 and 120 meters respectively when vehicle engine is off.
Figure 11B:
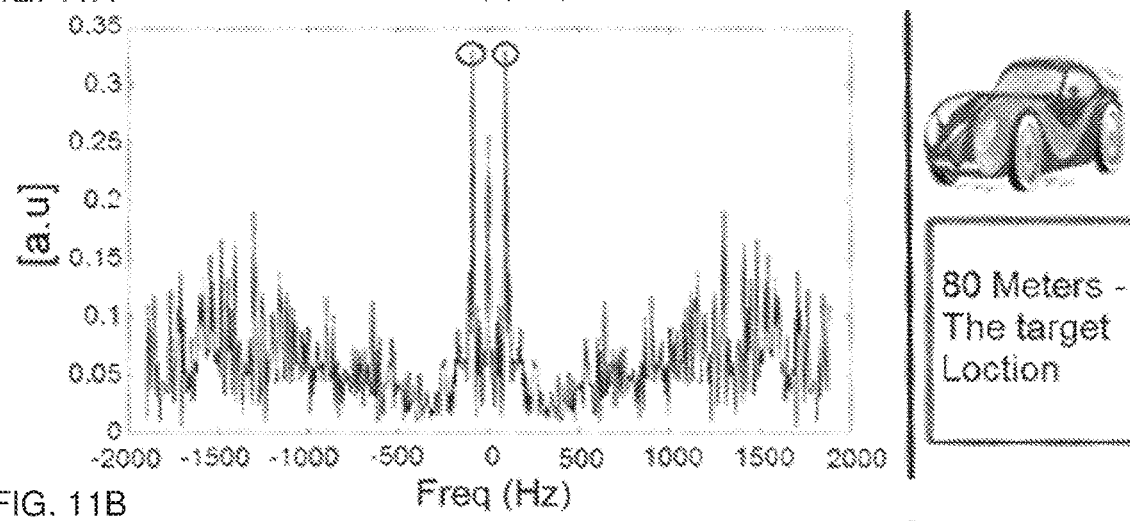
Figure 11C:
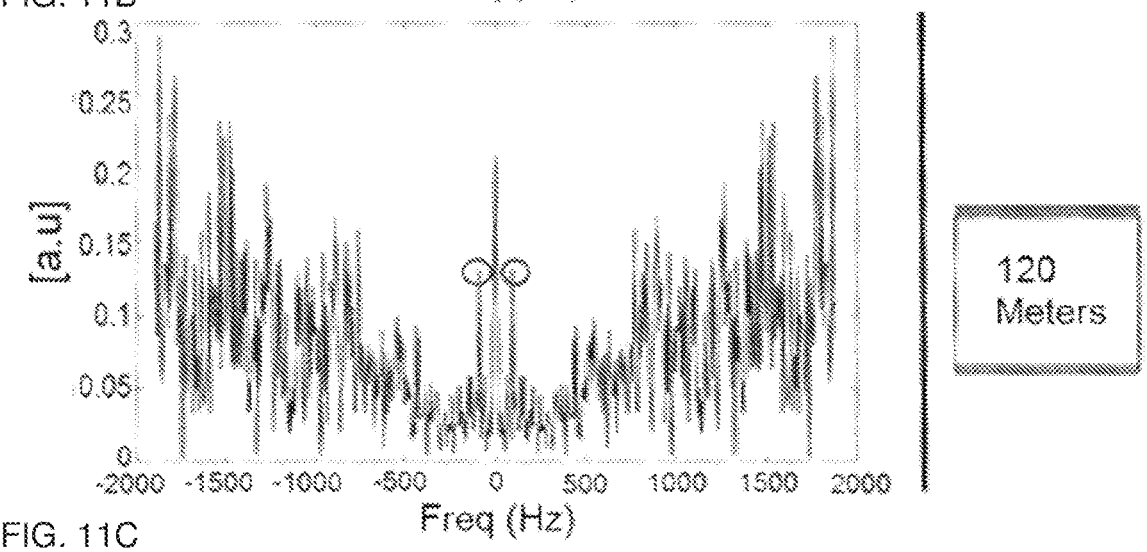
Figure 12A:
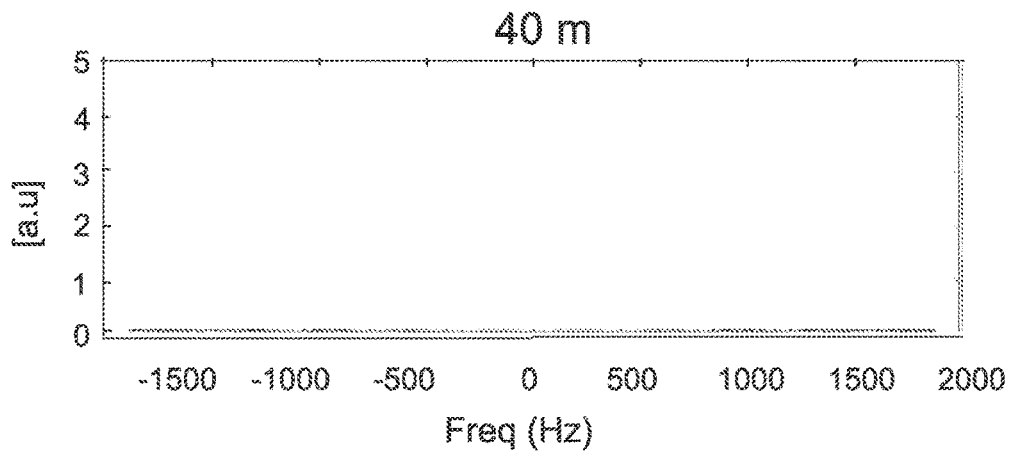
Figure 12B:
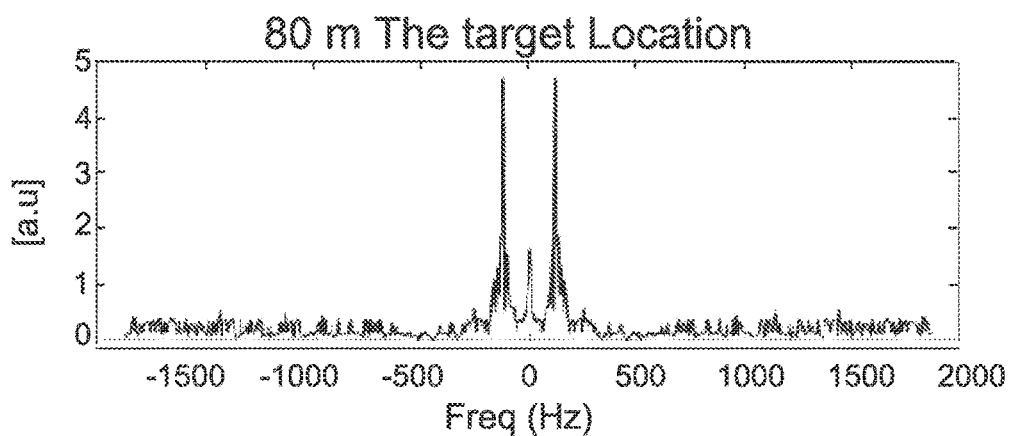
Figure 12C:
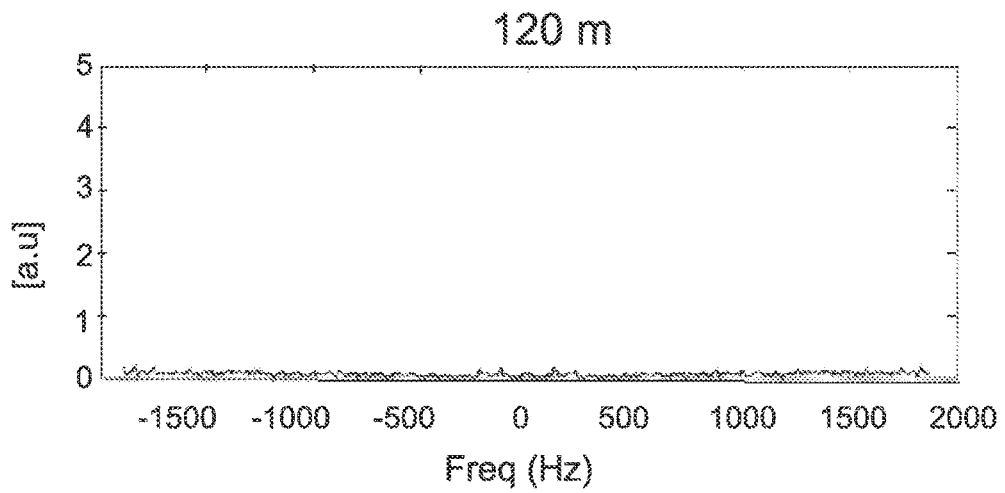

Reference is made to FIGS. 11A to 11C showing frequency response of the determined variation functions associated with ranges of 40, 80 and 120 meters respectively when the vehicle engine is off, and FIGS. 12A to 12C showing frequency response of the determined variation functions associated with ranges of 40, 80 and 120 meters respectively when the vehicle engine is on. FIG. 11A shows noise and general reflection as there is no specific target at range of 40 meters. FIG. 11B shows clear peaks associated with general reflection from the vehicle, while being around noise level. Additional peaks are shown in FIG. 11C, identified as being associated with vibrations of a fence located at about 120 meters. Generally, the vehicle can be detected, but no specific signal is provided when the engine is off. To contrast this detection, the response amplitude scale in FIGS. 12A to 12C is varied by a factor of 10 showing lower noise level. FIGS. 12A and 12C show no specific target, while FIG. 12B shows high response associated with vibrations of the vehicle due to its engine operation.

The maximum peak detected in FIG. 12B is located at 90 Hz when the signal is received from to the target having its engine on. The resulting peak is significantly higher than the peak measured when the engine was turned off. It should be noted that the results shown in FIGS. 11A-11C and 12A-12C do not include calculation of the Doppler Effect. The results of FIG. 11B show that also when the car engine ignition was off, the vibration of the car due to the wind was detected. However, as shown in FIG. 12B, the engine operation results in much stronger vibrations.

Additionally, the peaks shown in FIG. 11C, associated with vibrations of object at 120 meters are a result of a fence located at that distance, and represent vibrations of the fence due to wind. FIG. 12C shows that the fence vibrations are negligible with respect to the vibrations of the target when the engine ignition was on.

Figure 13:
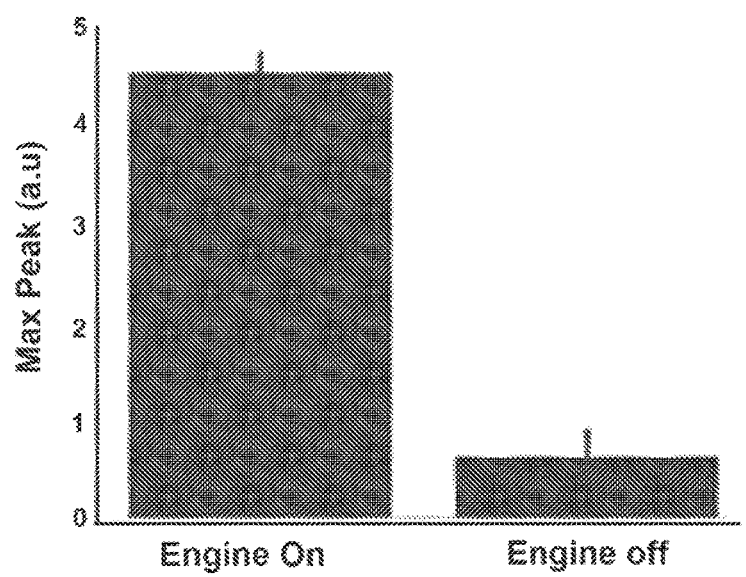
FIG. 13 shows difference between the maximum peaks while the vehicle's engine is turned on and off.

This experiment was repeated five times (each time the car was turned on and off). The difference between the maximum peaks while the car was turned on and off is shown in FIG. 13.

Accordingly, the present technique provides a system and method for monitoring parameters of an object by determining variations in RF speckle patterns reflected from the object. This technique enables monitoring from large distance, and even through walls without the need for obtaining direct optical line between the system and the object. The technique may be implemented using transmitting and collecting antenna arrangements operated by control system, e.g. computer system, utilizing signal processing techniques as described above.

The invention claimed is:

1. A system comprising:
RF transmission unit comprising an arrangement of one or more transmission antenna elements configured for transmitting radiation in one or more selected frequency ranges toward an inspection region;
RF collection unit comprising one or more collection antenna elements configured for receiving RF signals in said one or more selected frequency ranges from at least a portion of said inspection region; and
a control system configured for receiving and processing data on the RF signals received by the RF collection unit for determining one or more parameters on at least one object or at least one human located in said inspection region, wherein said control system comprises at least one processor configured for receiving and processing said data on the RF signals, said processing comprising determining at least one time shifting correlation function between the RF signals received at selected sampling rate, said at least one time shifting correlation function being indicative of variations in secondary speckle patterns in the RF signals returned from the at least one object or at least one human in the inspection region.

2. The system of claim 1, wherein said one or more parameters comprise one or more parameters associated with micro vibrations of the at least one object or human.

3. The system of claim 1, wherein said one or more parameters comprise parameters in-indicative of at least one of heart rate and breathing rate of the at least one human located in the inspection region.

4. The system of claim 1, wherein said control system comprises at least one storage utility comprising pre-stored data on one or more object vibration models; said at least one processor being configured for retrieving data on one or more of said object vibration models and for processing said at least one time shifting correlation function in view of said one or more object vibration models for determining one or more selected parameters of the at least one object or at least one human in the inspection region.

5. The system of claim 1, wherein said RF transmission unit comprises an arrangement of two or more antenna elements configured for transmitting selected RF signal with corresponding phase shifts between the two or more antenna elements to provide transmission of radiation toward a selected inspection region.

6. The system of claim 1, wherein said RF collection unit comprises an arrangement of two or more antenna elements, said control system comprises phase relation module configured for receiving collected signals from said two or more antenna elements and for determining phase relations between the collected signals associated with input signal arriving from a selected direction where the at least one object or at least one human is located.

7. The system of claim 6, wherein said control system is configured and operable for processing input RF signals from said two or more antenna elements and determining at least one time shifting correlation function between RF signals being indicative of spatial changes in collected RF pattern along time, said spatial changes being indicative of variations in secondary speckle patterns in radiation returned from the at least one object or at least one human.

8. The system of claim 7, wherein said control system is configured for using polynomial estimation for determining said spatial changes in collected RF patterns associated with spatial distance smaller than distance between said antenna elements.

9. The system of claim 1, wherein said RF collection unit comprises a single antenna element, said control system being configured for determining time variations in collected signal, being indicative of shifting in speckle patterns in radiation returned from the at least one object or at least one human.

10. The system of claim 1, wherein said RF collection unit is configured for providing pulsed RF transmission enabling detection of range of the at least one object or at least one human to be located using time difference between transmission and collection of the RF radiation.

11. A method for monitoring parameters of at least one object or human, the method comprising:
providing and transmitting RF radiation toward an inspection region where the at least one object or human is located, and collecting RF signals returning from the inspection region after reflection and scattering from the at least one object or human in the inspection region and generating data on collected RF signals;

processing said data on the collected RF signals, said processing comprising determining at least one time shifting correlation function between the collected RF signals being received at selected sampling rate, said at least one time shifting correlation function being indicative of variations in secondary speckle patterns in the collected RF signals reflected and scattered from the at least one object or human in the inspection region;

utilizing one or more object vibrations models and processing said at least one time shifting correlation function for determining one or more parameters of the at least one object or human in the inspection region.

12. The method of claim 11, further comprising providing one or more metallic elements on said at least one object or human, thereby increasing sensitivity for monitoring small vibrations of said at least one object or human.

13. The method of claim 11, wherein said at least one time shifting correlation function is indicative of small vibrations or movements of the at least one object or human, said small vibrations or movements being indicative of acoustic sounds generated by the at least one object or human.

14. A system comprising:
RF transmission unit comprising an arrangement of one or more transmission antenna elements configured for transmitting radiation in one or more selected frequency ranges toward an inspection region;

RF collection unit comprising an arrangement of two or more antenna elements each configured for receiving RF signals in said one or more selected frequency ranges from at least a portion of said inspection region; and a control system configured for receiving and processing data on the RF signals received by the RF collection unit for determining one or more parameters of at least one object or human located in said inspection region, wherein said control system comprises:

a phase relation module configured for receiving collected signals from said two or more antenna elements and for determining phase relations between the collected signals associated with input signal arriving from a selected direction where the at least one object or human is located; the control system being configured and operable to process the RF signals from said two or more antenna elements and determine at least one time shifting correlation function between RF signals being indicative of spatial changes in collected RF pattern along time, said spatial changes being indicative of variations in secondary speckle patterns in radiation returned from the at least one object or human.

15. The system of claim 14, wherein said control system is configured for using polynomial estimation for determining said spatial changes in collected RF patterns associated with spatial distance smaller than distance between said two or more antenna elements.

16. The system of claim 14, wherein said control system is configured to communicate with at least one storage utility comprising pre-stored data on one or more object vibration models; said at least one processor being configured for retrieving data on one or more of said object vibration models and for processing said at least one time shifting correlation function in view of said one or more object vibration models for determining one or more selected parameters of the at least one object or human in the inspection region.

17. The system of claim 14, wherein said RF transmission unit comprises an arrangement of two or more transmission antenna elements configured for transmitting selected RF signal with corresponding phase shifts between the two or more transmission antenna elements to provide transmission of radiation toward the selected inspection region.

* * * * *